United States Patent [19]

Kruger

[11] 4,097,477

[45] Jun. 27, 1978

[54] STEROID COMPOUNDS AND PROCESSES THEREOF

[75] Inventor: Gunther Kruger, St. Laurent, Canada

[73] Assignee: Steele Chemicals Co. Ltd., Pointe Claire, Canada

[21] Appl. No.: 703,825

[22] Filed: Jul. 9, 1976

Related U.S. Application Data

[63] Continuation-in-part of Ser. No. 516,597, Oct. 21, 1974, abandoned.

[30] Foreign Application Priority Data

Nov. 29, 1973 Canada .................................. 186960

[51] Int. Cl.² .......................... C07J 17/00; C07J 19/00
[52] U.S. Cl. ....................... 260/239.57; 260/239.55 R
[58] Field of Search ................... 260/239.57, 239.55 R

[56] References Cited

U.S. PATENT DOCUMENTS 3,812,106  5/1974  Stache et al. .................... 260/239.57
3,859,272  1/1975  Stache et al. .................... 260/239.57

*Primary Examiner*—Elbert L. Roberts
*Attorney, Agent, or Firm*—McFadden, Fincham & Co.

[57] ABSTRACT

Novel steroids of the formula

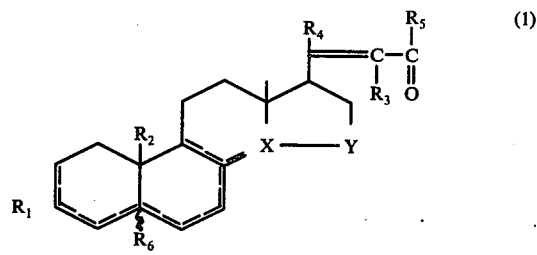

Also there are provided processes for preparing such compounds. The new compounds are useful as intermediates in the preparation of known cardenolides; various of the compounds have other uses as blocking agents.

17 Claims, No Drawings

STEROID COMPOUNDS AND PROCESSES THEREOF

This application is a continuation-in-part of United States application Ser. No. 516,597, filed Oct. 21, 1974, now abandoned.

This invention relates in one embodiment to new steroid compounds, and in a further embodiment, to processes for preparing steroid compounds.

More particularly, according to one embodiment of the present invention, there are provided new compounds of the formula

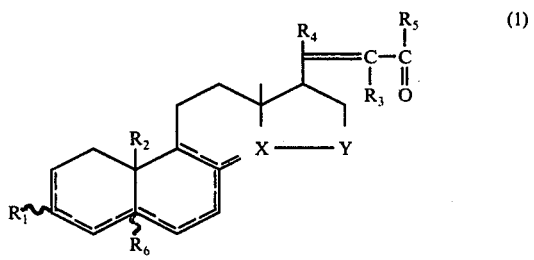

wherein $R_1$ to $R_6$ and X - Y have the meanings defined below, and wherein the dotted lines represent optional double bonds. In the embodiment where the 3 and 5 positions of these compounds are saturated, the substituents $R_1$ and $R_6$ may either be in the alpha or beta positions.

For a greater understanding of the present invention, the novel compounds may be classified as being of one of two groups of compounds, in which according to one embodiment, the componds of Formula 1 have saturated A, B, C and D — rings and in which $R_1$ represents either hydroxy or OAc, $R_2$ represents $CH_2OH$ or CHO, $R_3$ is H, $R_4$ and $R_5$ are $Ch_2$—O, $R_6$ is either R$\alpha$ or 5$\beta$-H, and X and Y together represent

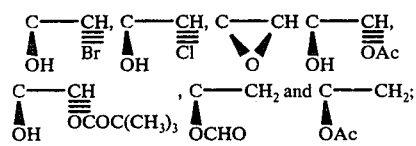

alternatively, the compounds according to a further embodiment are those compounds in which $R_1$ represents H, O=, $HCO_2$, $(CH_3)_3CCO_2$, $Cl_3CCO_2$, $(C_2H_5O)_2$-$P(O)CH_2CO_2$,

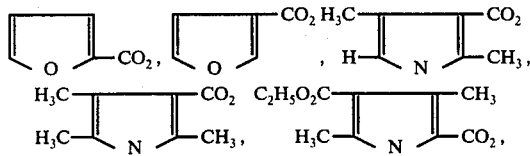

HC≡C-$CO_2$, $H_2$C=CH-$CO_2$, (HO)($CH_3$)CH $CO_2$, (HO)($CH_3$)$_2$C$CO_2$, $HO_2$C(CHOH)$_2$$CO_2$, $HO_2$C($CH_2$)$_2$-$CO_2$, $HO_2$C$CH_2$$CO_2$, $CH_3$O, ($CH_3$)$_3$CO, $C_6H_5CH_2$O, HC≡C$CH_2$O, tetrahydropyran-2-yloxy, 3$\alpha$, 9$\alpha$-oxido and 3-hydroxy-3$\alpha$,9$\alpha$-oxido, $R_2$ represents $HCO_2CH_2$, ($CH_3$)$_3$CC$O_2CH_2$; $Cl_3$CC$O_2CH_2$; ($C_2H_5$O)$_2$P(O)$CH_2$-$CO_2CH_2$;

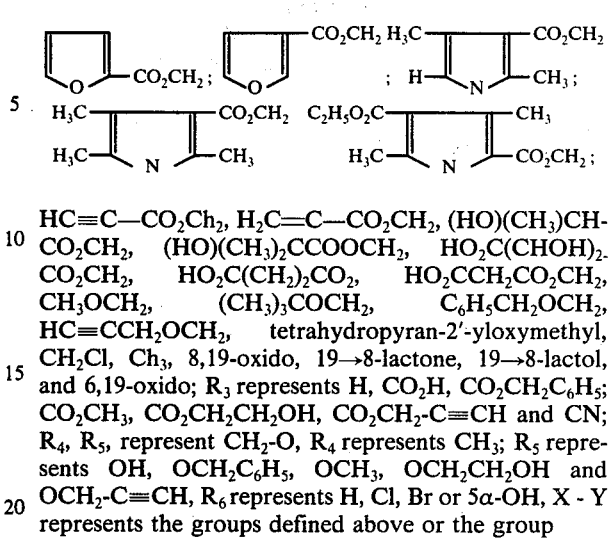

HC≡C—$CO_2Ch_2$, $H_2$C=C—$CO_2CH_2$, (HO)($CH_3$)CH-$CO_2CH_2$, (HO)($CH_3$)$_2$CCOOCH$_2$, $HO_2$C(CHOH)$_2$-$CO_2CH_2$, $HO_2$C($CH_2$)$_2$C$O_2$, $HO_2$CC$H_2$C$O_2CH_2$, $CH_3OCH_2$, ($CH_3$)$_3$COC$H_2$, $C_6H_5CH_2OCH_2$, HC≡CC$H_2OCH_2$, tetrahydropyran-2'-yloxymethyl, $CH_2$Cl, $CH_3$, 8,19-oxido, 19→8-lactone, 19→8-lactol, and 6,19-oxido; $R_3$ represents H, $CO_2$H, $CO_2CH_2C_6H_5$; $CO_2CH_3$, $CO_2CH_2CH_2OH$, $CO_2CH_2$-C≡CH and CN; $R_4$, $R_5$, represent $CH_2$-O, $R_4$ represents $CH_3$; $R_5$ represents OH, $OCH_2C_6H_5$, $OCH_3$, $OCH_2CH_2OH$ and $OCH_2$-C≡CH, $R_6$ represents H, Cl, Br or 5$\alpha$-OH, X - Y represents the groups defined above or the group

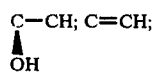

or CH—$CH_2$; and wherein double bonds may be present in the 2,4,6,8(14)-; 4,6,8(14)-; 4,6,8(9)-; 4,6-; 4-; 5; 5,7-; and 3,5,7-positions.

Particularly preferred embodiments of the present invention are compounds which can be expressed as follows:

A steroid of the formula

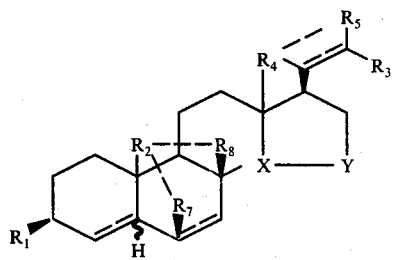

wherein the dotted lines represent covalent bonds which may or may not be present; wherein the group at the 17 $\beta$-position $R_3$ is H, $CO_2$H, $CO_2CH_2C_6H_5$, $CO_2CH_3$, $CO_2CH_2CH_2OH$ or CN, wherein, in the case of there being a bond between $R_4$ and $R_5$, the latter represent

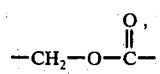

respectively, wherein, in the case of the absence of a bond between $R_4$ and $R_5$, $R_4$ is $CH_3$ and $R_5$ is selected from the $R_3$ group; wherein in the steroid nucleus $R_1$ is H, OH,

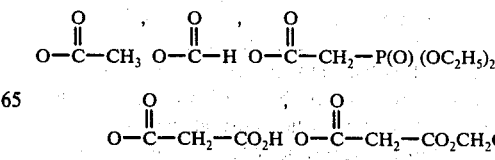

, or

-continued

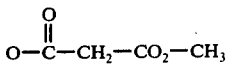

with the proviso that $R_1$ is not O, OH or an acyloxy group, in the case the 17β-group

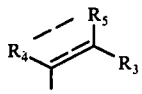

represents an unsubstituted butenolide ring

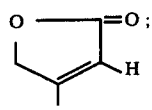

wherein, in the case of there being a bond between $R_2$ and $R_7$ or $R_2$ and $R_8$ the latter represents a 6,19-oxide, an 8,19-oxide or a 19 → 8 lactone group, respectively; wherein, in the case of there being no bond between $R_2$ and $R_7$, or $R_2$ and $R_8$, $R_2$ stands for $CH_2OH$, CHO,

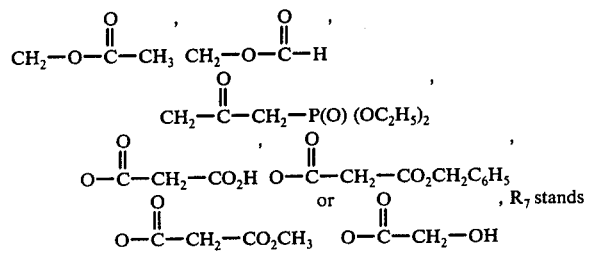, $R_7$ stands for H and $R_8$ stands for OH or H wherein, in the case of the 5-position being saturated, there may either be present a 5β- or 5α-hydrogen atom; wherein, as regards the substitutent in the steroid nucleus at the 14- or 15-position, X-Y stands for C(β-OH)-$CH_2$, C(β-OH)-CHBr, C(β-OH)-CHCl, C(α-OH)-$CH_2$, a β-oxide, an α-oxide, a double bond, C(α-H)$CH_2$ or C(β-H)-$CH_2$.

Other preferred embodiments of the compounds of the above formula are those compounds wherein the steroid is selected from the group consisting of carda-14,20(22)-dienolide; carda-4,20(22)-dienolide group; 19-oxygenated-14-hydroxy-5α, 14β-card-20(22)-enolide; or 19-oxygenated-14-hydroxy-5β, 14β-card-20(22)-enolide.

Other embodiments relate to compounds of the above formula in which the steroid contains a member selected from the group consisting of 6,19-oxido substituent; 8,19-oxido substituent; 3β-acetoxy substituent; 22-cyano substituent; 22-benzyloxycarbonyl substituent; 3β-acetoxy substituent; 19-formyloxy substituent; 19-hydroxy substituent; 22benzyloxycarbonyl substituent; card-20(22)-enolide; 14,15 β-oxido group, 19- formyloxy substituent; 14-hydroxy substituent; 14β, 19-dihydroxy substituents; 3β-acetoxy substituent; or 3β, 19-diacetoxy substituents.

A still further embodiment of the compounds of the above formula is where there is provided a 3-deoxy steroid having an $R_1$ substituent in the 3-position which is a hydrogen atom and in which the 19-position carries an oxygen function; and in other embodiments, and in such a case, the steroid preferably contains the group in which the substituent $R_1$ at the 3-position is a hydrogen atom and in which the 19-position carries an oxygen function. Still further, preferably the crotonic acid or crotonic acid derivative carries as group $R_3$ a carboxylic acid group or a derivative thereof. In this group of compounds, preferably the 8β-position is linked to the 19-position by an oxygen atom and in which A-B stands for a double bond or an α-oxide; there may be further included an oxide in the 6,19-position or in the 14,15-position - and there may be a hydroxy group in the 14β- and a halogen atom in the 15α-position.

In accordance with a further aspect of the present invention, there are provided processes for preparing the above compounds and compounds generally of the formula

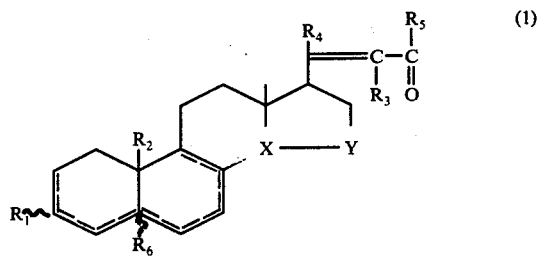

wherein $R_1$ through $R_6$, X and Y have the above-defined meanings and additionally may represent, when the A, B, C, and D rings of the compounds are saturated, compounds in which X and Y are

or C=$CH_2$, $R_1$ is OH or Ac, $R_2$ is $CH_2OH$ or CHO, $R_3$ is H and $R_{4,5}$ is $CH_2O$; in accordance with this embodiment of the invention, the process is selected from the group consisting of (a) treating a compound of the formula 2

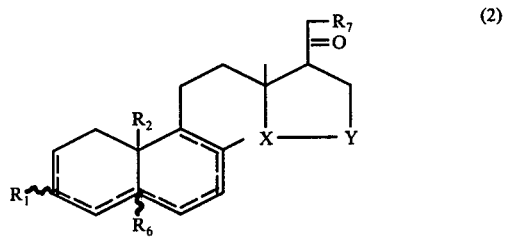

wherein $R_1$, $R_2$, $R_6$, X and Y and the dotted lines are as defined above, and $R_7$ is OH; with an α-substituted acetic acid to form a compound of the formula(3)

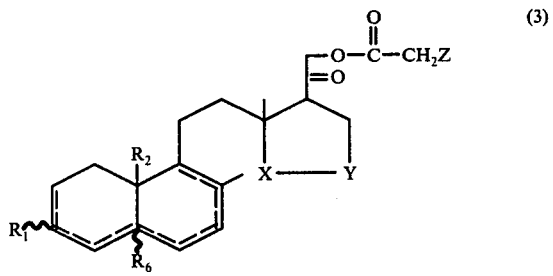

wherein $R_1$, $R_2$, $R_6$, X and Y and the dotted lines are as defined above and wherein Z is a substituent chosen from those enhancing the acidity of the adjacent methylene group; and finally treating the compound of the formula (3) with a base to form a compound of the formula (1), in which $R_1$, $R_2$, $R_3$, $R_6$, X and Y and the double bonds are as defined above and in which $R_4$ and $R_5$ are $CH_2$—O;

(b) treating a compound of the formula (2) in which $R_7$ is OH, $OCOCH_3$ or H, with an alkali alkoxyacetylide and then with an alcohol or water to form an intermediate compound of the formula (4)

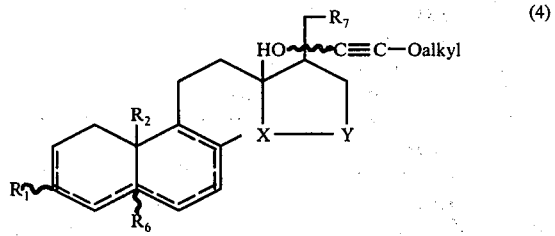

wherein $R_7$ is OH or H and in which alkyl is $CH_2H_5$, $CH_3$ or $CH_2C_6H_5$, subjecting the latter compound to acid treatment to form a compound of the formula (1) in which $R_3$ is H and $R_4$, and $R_5$ is $CH_2$—O— when $R_7$ in the compound of formula (4) is OH, or in which $R_3$ is H, $R_4$ is $CH_3$ and $R_5$ is $OCH_2H_5$, $OCH_3$ or $OCH_2C_6H_5$ when $R_7$ in the compound of formula (4) is H;

(c) treating a compound of the formula (1) in which $R_1$, $R_2$, $R_6$, X and Y and the dotted lines are as defined above, while $R_4$ and $R_5$ represent $CH_2$—O and $R_3$ represents $CO_2H$, $CO_2CH_2C_6H_5$; $CO_2CH_3$; $CO_2CH_2CH_2OH$ or $CO_2CH_2$-C≡CH, with zinc and a carboxylic acid to form a compound of the formula (1), in which $R_3$ represents a member selected from the group consisting of $CO_2H$, $CO_2CH_2C_6H_5$, $CO_2CH_3$, $CO_2CH_2CH_2OH$ and $CO_2CH_2$—≡CH; $R_4$ is $CH_3$, and $R_5$ is OH, $OCH_2CH_2C_6H_5$, $OCH_3$, $OCH_2CH_2OH$ or $OCH_2$-C≡CH.

In greater detail of the above processes, the conversion of the 21-alcohols of the formula (2), where $R_7$ is OH, to the corresponding compounds of formula 1 by process (a) is most preferably carried out by treatment of the 21-alcohols with an α-substituted acetic acid, such as (diethylphosphono) acetic acid, (benzyloxycarbonyl) acetic acid or cyanoacetic acid in the presence of a carbodiimide (for example, dicyclohexylcarbodiimide and a water immiscible solvent such as methylene chloride or benzene, and subsequent treatment of the resulting reaction mixture containing 21-acylate (3) as an intermediate with a water stable base- for example aqueous potassium hydroxide or aqueous or anhydrous t-butylamine. The reaction is preferably carried out at room temperature, though higher or lower temperatures may be employed if desired.

In an alternate embodinent of the above process (a), the 21-alcohol may be heated between 50 to about 150° C. with the corresponding β-substituted acetic acid in the presence of a ketonic solvent, sich as acetone or methyl isobutyl ketone. Where the radical Z is $CO_2H$, the resulting 21-hemimalonate may be then esterified by a suitable conventional technique - such as for example, to treatment with an appropriate diazoalkane, such as diazomethane or diazotoluene to yield compounds of the formula (3) in which Z is $CO_1alkyl$. Similarly, in a related embodiment of process (a), the 21-alcohol may be treated with a derivative of an α-substituted acetic acid, such as an acid chloride, $ZCH_2COCl$ anhydride, $(ZCH_2CO)_2O$, mixed anhydrides, $ZCH_2CO$—O—OCR, wherein Z is as defined above and R is $(CH_3)_3C$, $F_3C$ or $Cl_3C$, or ester, $ZCH_2CO_2alkyl$, wherein alkyl is $CH_3$, $C_2H_5$, $CH_2C_6H_5$ or $CH_2$-C≡CH. In the case where the carboxylic acid derivative is an acid chloride, or an anhydride or mixed anhydride, the treatment may be carried out at room temperature in the presence of a mold base such as pyridine; in the case where the carboxylic acid derivative is an ester the conversion to the 21-acylate may be brought about by heating the 21-alcohol with the ester at a temperature of between about 50° to 220° C. The base treatment of process (a) may be preferably carried out with a strong aqueous base such as 1 – 80% aqueous potassium or sodium hydroxide.

The treatment of the 21-alcohol or 21-acetate of process (b) with an alkali alkoxy acetylide may be carried out as described by F. Sondheimer, Chemistry in Britain, 1, 454 (1965); preferably it may be carried out at room temperature in an anhydrous ether such as diethyl ether or tetrahydrofuran and as the alkali alkoxy acetylide lithium methoxy. Alternatively, ethoxyacetylide may be employed. The subsequent acid treatment may also be carried out at room temperature. Dilute aqueous strong inorganic acids, such as hydrochloric, sulfuric or perchloric acid are preferably employed as the acid; while as the solvent for the intermediate steroidal 20-alkoxyethylnyl-20-alcohol of formula 4 a water-immiscible solvent, such as benzene, either or methylene chloride, is preferably used.

The treatment of the 22-substituted cardenolide of process (c) with zinc and a carboxylic acid may be preferably carried out at room temperature in the presence of an inert solvent such as toluene, methylene chloride or ethyl acetate and the carboxylic acid formic acid, acetic acid and substituted acetic acids such as trimethylacetic or trifluoroacetic acid may be employed.

The various processes of the present invention possess several unexpected and advantageous features. Thus, with regard to process (a) it is unexpected that the esterification of the 21-alcohol to compounds of formula (2), in which Z is $CO_2H$, gives improved yields when ketonic solvents, such as methyl isobutyl ketone, are used and that the esterification proceeds in a highly selective manner, yielding practically only the 21-hemimalonate, in which one of the 2-carboxylic acid groups of the malonic acid employed as the reagent remains still unreacted.

With regard to process (a) it is also unexpected that the conversion of the 21-(dialkylphosphono)acetates of formula (3), Z being (alkyl)P(O) to the corresponding cardenolides of formula (1), $R_3$ being H, $R_4$, $R_5$ being $CH_2O$ can be effected by a base of only moderate basic strength, such as an aqueous alkali hydroxide or alkylamine since this conversion is a phosphonate modification of the Wittig reaction (see for example L. F. Fieser and M. Fieser, John Wiley and Sons, Inc., 1967, p. 1319 and 251) and hence, according to the prior art of carrying out Wittig reactions, requires a very strong base such as n-butyl lithium, sodium hydride and potassium t-butoxide (ibid. p 1319), as one of the reagents. In contrast to the moderate bases of this invention, the latter, very strong bases have in common that they are rapidly destroyed by water.

It is further unexpected that the above conversion of formula (3) to formula (1) can be accomplished by employing a water-immiscible, non-polar solvent, such as benzene as the solvent for the steroid. As is well known to those skilled in the art, reactions being brought about by the action of a chemical reagent are generally greatly enhanced when the reagent is soluble in the solvent employed for the dissolution of the reactant.

It is also unexpected and a novel feature of process (a) that the conditions developed for the conversion of compounds of formula (3), Z being (alkyl)P(O), to compounds of formula (1), $R_3$ being H, are also very suitable for the conversion of compounds of formula (3), where Z is CN and $CO_2$alkyl to compounds of formula (1), where R is CN and $CO_2$alkyl. The latter type of conversion is no longer a Wittig reaction but resembles the Knoevenagel condensation (see for example R. C. Denney "Denney Organic Reactions", Butterworth, London 1969, p 50).

The wide scope of process (a) owing to which it can be applied to 21-esters of formula (3) in which Z is not only (alkyl)P(O) but also CN and $CO_2$alkyl, is a special advantage of this process.

It is another advantage of the process (a) of this invention that the conversion of (3) to (1) can readily be brought about by bases of only moderate strength as this allows the transformation of reactants possessing groups which would be chemically changed if the usual stronger bases of a Wittig reaction were used.

It is a further advantage of process (a) that the formation of the phosphonoacetate (3) from 21-alcohol (2) and the conversion (3) to (1) can be carried out in one vessel and that no intermittent evaporations of solvents are used in the two conversions are required. It is yet another advantage that, since the moderately strong bases employed in this invention are not affected by water, no special precautions have to be observed to ensure that the conversion of (3) to (1) is carried out under anhydrous conditions. The conversion of (3) to (1) via (2) can thus be carried out in a manner which is considerably more simple and economical than the previous procedure of choice of converting 21-hydroxy-20-ones of the pregnane series to cardenolides (see W. Eberlein, J. Nickl, J. Heider, G. Johns and H. Machleidt, Chem. Ber., 105, 3686 (1972). who prepared 22-halo, alkyl- and alkoxycardenolides).

It is an advantage of process (b) that the conversion of the alkyloxyacetylene adduct (4) to the corresponding 20(22)-en-23-oic acid esters or cardenolides of formula (1), respectively, can be brought about treatment of a solution of (4) in a water immiscible inert solvent, (e.g. benzene, hexane, or ether) with a dilute aqueous solution of a mineral acid, such as perchloric, hydrochloric or sulfuric acid. By contrast in the previous method of converting the adduct (4) to the ester (1) the latter are treated with a mixture of an alcohol and aqueous sulfuric acid. Since alcohols in the presence of acid are not inert solvents, e.g. they may cause an exchange of the alkoxy group in esters 1 (F. S. Khristulas, M. B. Gorovich and N. K. Abubakirov, Khimya Prirodnikh Soedinenii, 5, 545 (1970) p 551), the method of this invention employing inert solvents for the above conversion has a greater synthetic utility. Further enhanced utility derives from the fact that in the method of this invention the reaction products can be more readily isolated from the reaction mixture, i.e. by the simple procedure of extracting the organic, water immiscible phase with water till the extracts are neutral and subsequent evaporation of the inert solvent. Yet further utility derives from the fact that the method is more applicable to such compounds of formula (4), which are not soluble or only partially soluble in the acidic aqueous alcohol employed in the prior art. As is well known, steroids are generally more soluble in water immiscible organic solvents than in aqueous alcohols.

With regard to process (c), it is submitted that there is no prior art which teaches the conversion of cardenolides into the corresponding 22-alkoxycarboxyl-21-methyl-20(22)-en-23-oic acids or the corresponding 23,24-dioc acids, such as represented by formula (1), where $R_3$ is an alkoxycarbonyl, $R_4$ is methyl group and $R_5$ is the hydroxy group of a carboxylic acid. It is a special advantage of process (c) that it provides stereospecific routes towards (22-E) and (22-Z) 22-substituted 20(22)-enes. By contrast, no such stereo-specific routes are provided for by the previous methods of preparing 21-methyl-22-substituted 20(22)-enes the stereochemistry of which is generally left unspecified (see, for example, F. Sondheimer and F. S. Khristulas, cited above, and also M. Okada and Y. Saito, Chem. Pharm. Bull., 16, 2223 (1968)).

Many of the products of the present invention of formula (1) have been found to have smaller properties to the compounds of forumla

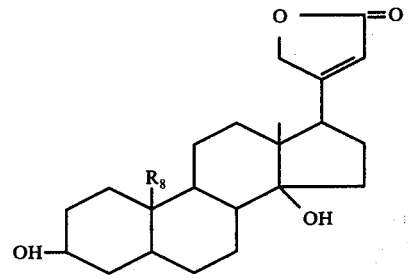

wherein $R_8$ is chosen from the group of H, $CH_2OH$, $CH_2$—O—CO— NH—$C(CH_3)_3$, $CH_2Oalkyl$ and $CH_2Oacyl$, wherein alkyl is tetrahydropyranyl, lower alkyl, preferably methyl, or a substituted methyl wherein the substituent is selected from the group consisting of phenyl, halogen, preferably chlorine and bromine, methoxy, $CH_2$=CH and HC≡C, and wherein acyl represents a group selected from those consisting of acetate, lower trialkyl acetates wherein the lower alkyl group is preferably methyl or ethyl, monohalo acetates and trihalo acetates, preferably wherein the halogen is chlorine, fluorine and bromine. The compounds of the above formula and their glycosides are known for treatment of cardiac insufficiency, as for example disclosed in Angewandte Chemie vol. 9, No. 5, pp 321-332, and Fieser and Frieser, Chap. 20, "Steroids", Reinhold, NY 67. In addition, the compounds of formula (1) may in some cases be also used as intermediates for the preparation of compounds of the above given formula, by converting the compounds of formula (1) by conventional techniques, or alternatively, by methods similar to those described in the following Examples. Still further, certain of the compounds of formula (1) — i.e. those without a 14β oxygen, may be useful as modifiers of cardiatonic compounds - e.g. by suppresing selectively their toxic activity. Those compounds not having a 3 oxygenated substituent have similar properties to the known compounds or 3-deoxy analogs, 17 analogs in which the 17 substituent is a 20(22)-en-23-oic acid ester derivative or the 22 substi-

EXAMPLE 1

A mixture, prepared by successive addition of 3.942 ml of a 10% solution of [diethylphosphono]acetic acid (1.3 moles per mole of 21-hydroxy-20-ketone) in benzene and 10.05 ml of a 0.2 molar solution of dicyclohexylcarbodiimide (1.3 moles per mole of 21-hydroxy-20-ketone) in benzene to a solution of 600 mg of 3β-acetoxy-21-hydroxy-8,19-oxido-5α-pregn-14-en-20-one in 30 ml of benzene, was stirred under nitrogen at room temperature for 18 minutes, whereupon a small fraction was withdrawn and added to 1 volume of water. Evaporation of the organic phase gave 3β-acetoxy-21-[diethylphosphono]acetoxy-8,19-oxido-5α-pregn-14-en-20-one as evidenced by tlc analysis and subsequent transformations.

The remaining major reaction mixture was stirred under nitrogen with 15 ml of 50% aqueous potassium hydroxide for 15 minutes at room temperature, whereupon 75 ml of a mixture of water and ice was added. Acidification of the mixture with acetic acid-water 1:10, followed by dilution with ether-methylene chloride 4:1, five extraction of the organic phase with 1/4 volume of water, evaporation at reduced pressure and drying at high vacuum gave a residue which was stirred with 30 ml of methylene chloride under nitrogen for 15 minutes. The undissolved solid was then removed by filtration. Concentration of the filtrate, followed by addition of hexane till a faint turbidity appeared, filtration through diatomaceous earth, concentration of the filtrate at reduced pressure with intermittent addition of hexane and ether, standing at −5° C for 2 hours and filtration gave 524 mg of 3β-acetoxy-8,19-oxido-5α-carda-14,20(22)-dienolide, mp 214,220°–221° C. Recrystallisation from methanol water gave a purified sample, mp 219,222°–224° C. uv (MeOH) 219 mμ

EXAMPLE 2

A mixture, prepared by successive addition of 17.7 mg of [diethylphosphono]acetic acid (2.6 moles per mole of 3,21-diol), 0.175 ml of benzene and 0.455 ml of a 0.2 molar solution of dicyclohexylcarbodiimide (2.6 moles per mole of 3,21-diol) in benzene to a suspension of 12mg of 3β,21-dihydroxy8,19-oxido-5α-pregn-14-en-20 -one in 0.175 ml of benzene, was stirred under nitrogen at room temperature. Tlc analysis on a sample withdrawn after 20 minutes indicated that all starting material had been converted to 3β,21-di[diethylphosphono]-acetoxy-8,19-oxido-5α-pregn-14-en-20-one.

After 35 minutes of stirring 0.115 ml of 50% aqueous potassium hydroxide was added and stirring was continued for 30 minutes, whereupon 0.455 ml of water was added. The mixture was then filtered, the phases were separated, the aqueous phase of the filtrate was acidified. Filtration of the resulting precipitate yielded 3β-[diethylphosphono]acetoxy8,19-oxido-5α-carda-14,20(22)-dienolide, uv(MeOH) 219 mμ, ir (KBr) 3070, 1777, 1748, 1628, 1110, 1050, 1003, 926, 890, 860 and 818 cm$^{-1}$.

EXAMPLE 3

A mixture, prepared by successive addition of 3.35 ml of a 0.2 molar solution of dicyclohexylcarbodiimide (1.3 moles per mole of 21-hydroxy-20-one) in benzene to a solution of 130 mg of benzyl hemimalonate (1.3 moles per mole of 21-hydroxy20-one) and 200 mg of 3β-acetoxy-21-hydroxy-8,19-oxido-5α-pregn-14-en-20-one in 10 ml of benzene, was stirred under nitrogen at room temperature. Tlc analysis on a sample withdrawn after 15 minutes indicated that all starting material had been converted to 3β-acetoxy-21-[benzoyloxycarbonyl]-acetoxy8,19-oxido-5α-pregn-14-en-20-one.

The mixture was then stirred under nitrogen for 2-¼ hours with 2.5 ml of 10% aqueous potassium hydroxide, whereupon 4.0 ml of water and 2.0 ml of acetic acid-water 1:10 and 2 volumes of ether was added. The mixture was agitated and the fine, undissolved precipitate was removed by filtration. The organic phase of the biphasial filtrate was extracted 5 times with water and then evaporated. Recrystallisation of the residue from ether-hexane gave 216 mg of a precipitate which after a further recrystallisation from the same solvent system gave 3β-acetoxy-22-benzyloxycarbonyl-8,19-oxido-5α-carda-14,20(22)-dienolide, mp 174, 176°–178°C, uv (MeOH) 212 and 229 mμ.

EXAMPLE 4

When 40 mg of 3β-acetoxy-21-hydroxy-8,19-oxido-5α-pregn14-en-20-one as subjected to reaction conditions, which were essentially the same as those described in Example 3 except that cyanoacetic acid instead of benzyl hemimalonate was used, the 21-cyanoacetate of the starting material was obtained as the intermediate product, which after the base-treatment and chromatographic separation on silica gel G coated glass plates with ethyl acetate-benzene 1:1 as the eluant gave 3β-acetoxy-22-cyano-8,19-oxido-5α-carda-14,20(22)-dienolide, uv (MeOH) 210 and 234 mμ, and 22-cyano-3β-hydroxy-8,19-oxido-5α-carda-14,20(22)-dienolide, uv (MeOH) 209 and 234 mμ.

EXAMPLE 5

When 23 mg of 3β,19-diacetoxy-21-hydroxy-5α-pregn-14-en20-one was subjected to reaction conditions, which were essentially the same as those described in Example 1, except that, instead of 1.3 moles, 1.5 moles per mole starting material of [diethylphosphono]acetic acid and dicyclohexylcarbodiimide were used, the 21-[diethylphosphono]acetate of the starting material was obtained as an intermediate. The subsequent base-treatment, followed by chromatographic purification of the cruude product on silica gel coated glass plates, with ethyl acetate-benzene 1:7 as the eluant, and digestion of the purified material with pentane afforded 3β,19-diacetoxy-5α-carda-14,20(22)-dienolide, mp 155°–162° C.

EXAMPLE 6

When 97.38 mg of 19-acetoxy-21-hydroxy-pregna-4,6-diene-3,20dione was subjected to reaction conditions, which were essentially the same as those described in Example 1, except that 2.6 moles per mole of starting material of [diethylphosphono]acetic acid and dicyclohexylcarbodiimide were used instead of 1.3 moles each, the 21-[diethylphosphono]acetate of the starting material was obtained as an intermediate. The subsequent base-treatment, and chromatographic purification of the crude product on silica gel G coated glass plates, ethyl acetate-benzene 2:1 being the eluant, afforded 19-acetoxy-3-oxo-carda-4,6,20(22)-trienolide, mp 180,197°–199°, uv (MeOH) 218 and 285 mμ.

EXAMPLE 7

When 172.2 mg of 8,19-oxido-21-hydroxypregn-4-en-3,20-dione was subjected to reaction conditions which were essentially the same as those described in Example 6, except that the intermediate 21-[diethylphosphono]acetate of the starting material was isolated and separated from residual starting material by chromatography on silica coated glass plates and then subjected to the base-treatment, recrystallisation of the final crude product from ethyl acetate-pentane gave 36.3 mg of a crystalline material consisting essentially of 3-oxo-8,19-oxido-5α-carda-14,20(22)-dienolide containing a more polar alcohol as an impurity. Treatment of the latter product with pyridine-acetic anhydride at +5° C. for 2½ days, followed by addition of water, filtration and recrystallisation of the precipitate collected with methylene chloride-ether gave 18 mg of the purified product, mp 227, 228°–231° C., ir(NUJOL) 3105 (weak), 1778, 1745, 1670, 1622, 1375, 1305, 1258, 1045, 1020, 966, 890, 882 and 815 cm$^{-1}$.

EXAMPLE 8

When 400 mg of 3β-acetoxy-21-hydroxypregn-5-en-20-one was subjected to reaction conditions, which were essentially identical to those described in Example 1, 336 mg of 3β-acetoxycarda-5,20(22)-dienolide, mp 168, 169°–173° C., was obtained via the 21-[diethylphosphono]acetate of the starting material.

EXAMPLE 9

When 166.25 mg (0.5 millimoles) of 3β-21-dihydroxypregn-5-en-20-one was subjected to reaction conditions, which were essentially the same as those described in Example 2, the base-treatment of the intermediate 3β,21-di[diethylphosphono]-acetoxy-pregn-5-en-20-one gave 3β-[diethylphosphono]acetoxycarda-5,20(22)-dienolide, ir(KBr) 2970, 1785, 1755, 1730, 1635, 1260, 1250, 1145, 1120, 1070, 1025, 900, 875 and 790 cm$^{-1}$.

EXAMPLE 10

When 400 mg of 3β-acetoxy-21-hydroxypregn-5-en-20-one was treated under reaction conditions which were essentially the same as those described in Example 3 except that the intermediate 3β-acetoxy-21-[benzyloxycarbonyl]acetoxy-pregn-5-en-20-one was isolated and purified by precipitation with hexane from a methylene chloride solution, dissolution of the crude final product in methylene chloride, following by precipitation with hexane, gave 551 mg of 3β-acetoxy-22-[benzyloxycarbonyl]-carda-5,20(22)-dienolide as evidenced by the comparison with a sample of another batch, which had uv(MeOH) 216 and 230 mμ.

EXAMPLE 11

A mixture, prepared by successive addition of 118.8 mg of cyanoacetic acid (1.3 moles per mole of 21-hydroxy-20-ketone) and 6.96 ml of 0.2 molar solution of dicyclohexylcarbodiimide (1.3 moles per mole of 21-hydroxy-20-ketone) in benzene to a solution of 400 mg of 3β-acetoxy-21-hydroxypregn-5-en-20-one in 20 ml of benzene, was stirred under nitrogen. Tlc analysis on a sample within drawn after 80 minutes showed that all of the starting material had been converted to the corresponding 21-cyanoacetate. The mixture was stirred with 6.0 ml of 10% aqueous potassium hydroxide under nitrogen for 10 minutes, whereupon 160 ml of water and 200 ml of ether was added. The lower, aqueous phase was separated, acidified with 9.0 ml of 2N aqueous sulfuric acid and extracted with ether. The ether solution was extracted with water till the aqueous extracts were neutral, dried with sodium sulfate and evaporated at reduced pressure. Dissolution of the residue obtained in methylene chloride, addition of hexane till the solution became slightly turbid, filtration through diatomaceous earth, concentration of the filtrate with intermittent addition of hexane, standing at −5° C and filtration gave 355 mg of 3β-acetoxy-22-cyanocarda-5,20(22) dienolide, mp 200°–215°, uv(MeOH)241 mμ, as verified by ir- and nmr-spectroscopy.

Agitation of 34.4 mg of the above compound, dissolved in 3.45 ml of benzene, with 3.45 ml of 50% aqueous potassium hydroxide for 3 hours, followed by acidification with 2N aqueous sulfuric acid and isolation of the steroidal product by a procedure which was essentially the same as the one outlined above, gave 3β-hydroxy-22-cyanocarda-5,20(22) dienolide mp 211°–225°, uv(MeOH) 239 mμ, ir (KBr) 3550, 2225, 1760, 1640, 1065, 1045, 1025 and 760 cm$^{-1}$.

EXAMPLE 12

When 50 mg of 21-hydroxy-8,19-oxido-5α-pregn-14-en-20-one was subjected to reaction conditions which were essentially the same as those described in Example 1, 44 mg of 8,19-oxido-5α-carda-14,20(22) -dienolide, mp 177, 179–184° C, uv (CH$_3$OH) 218 mμ was obtained via the 21-[diethylphosphono]acetate of the starting material.

EXAMPLE 13

When 20 mg of 21-hydroxy-8,19-oxido-5α-pregn-14-en-20-one was subjected to reaction conditions which were essentially the same as those described in Example 4, 21-cyanoacetoxy8,19-oxido-5α-pregn-14-ene was obtained as the intermediate and 22-cyano-8,19-oxido-5α-carda-14,20(22) dienolide, ir (Kbr) 2220, 1774, 1625 and 1572 cm$^{-1}$ as the final product. A methanolic solution of the latter compound had uv 237 mμ; after addition of a small amount of aqueous potassium hydroxide it had uv 256 mu.

EXAMPLE 14

A mixture of 250 mg of 3β-acetoxy-8,19-oxido-5α-carda-14,20(22) -dienolide, 7.5 g of zinc, 18.75 ml of toluene and 6.25 ml of formic acid was shaken for 16 hours whereupon the supernatant phase was decanted. The residue was shaken briefly with 25 ml of benzene, which was then decanted. The benzene extraction was repeated another 4 times. The decanted supernatant liquids were filtered, combined and evaporated at reduced pressure. The residue was dissolved in methylene chloride and hexane was added to the solution till it became faintly turbid. The mixture was filtered through diatomaceous earth and the filtrate was concentrated at reduced pressure with intermittent addition of hexane and ether. Standing of the mixture at −5° C., followed by filtration gave 237 mg of 3β-acetoxy-19-formyloxy-5α-carda-14,20(22) -dienolide, uv(MeOH) 218 mμ, ir(KBr) 3065 (weak), 1795, 1767, 1740, 1730, 1640, 1255, 1207, 1170, 1141, 1081, 1059, 1030, 911, 895, 867, 815 and 745 cm$^{-1}$. TLC analysis showed that the reaction proceeds via 3β-acetoxy-19-hydroxy-5α-carda-14,20(22) -dienolide.

EXAMPLE 15

Reduction of 70 mg of 8,19-oxido-5α-carda-14,20(22)-dienolide with zinc in presence of formic acid under conditions which were essentially the same as those described in Example 14, afforded 39.8 mg of 19-hydroxy-5α-carda-14,20(22)-dienolide 19-formate, mp 131,135-136.5° C., via 19-hydroxy-5α-carda-14,20(22) -dienolide.

EXAMPLE 16

A mixture of approximatly 38 mg of 3β-acetoxy-8,19-oxido-5α-carda-14,20(22)-dienolide, 3.8 ml of glacial acetic acid, 0.97 ml of water and 77 mg of zinc dust was stirred briefly at room temperature and then with external heating by an oil-bath having a temperature between 65° to 69° C. After 5 minutes of stirring in the oil-bath, 388 mg of zinc was added slowly during 3 minutes followed by 3 further slow additions during 3-4 minutes of the same quantity of zinc after 36, 227 and 254 minutes respectively. The mixture was then filtered and the precipitate was washed with acetic acid-water 4:1 and ethyl acetate. The filtrate was concentrated 3 times at reduced pressure to ½ volume with intermittent addition of 3 × 30 ml of water. The resulting mixture was neutralized with a ½ saturated aqueous sodium bicarbonate and left to stand at +5° C for 2½ days. Filtration gave 28 mg of a product containing 3β-acetoxy-19-hydroxy-5α-carda-14,20(22)-dienolide as the major compound as evidenced by tlc. The latter material, 0.11 ml of pyridine and 0.056 ml of acetic anhydride was then left to stand under nitrogen for 16 hours at room temperature, whereupon it was diluted with hexane-ether 2:1 and filtered. The filtrate was concentrated at reduced pressure with intermittent addition of toluene. Chromatography of the resulting resin on silica gel G coated glass plates with ethyl acetate-benzene 1:4 as the eluant, followed by digestion with pentane of the fraction isolated, gave 10 mg of 3β,19-diacetoxy-5α-carda-14,20(22)-dienolide, mp 162,163°-164°, which as evidenced by its ir-spectrum and melting point, was found to be identical with β-anhydrocoroglaucigenin 3,19-acetate, mp 161°-163°, (A. Hunger and T. Reichstein, Helv., 35, 1073 (1952).

EXAMPLE 17

A mixture of 30 mg of 3β-acetoxy-19-formyloxy-5α-carda-14,20(22) -dienolide, 1.2 ml of acetone and 0.6 ml of a solution of 60 mg of N-bromoacetamide in 1 ml of water was stirred under nitrogen in the dark in an ice-bath for 97 minutes whereupon 18 ml of ice-water and 1.2 ml of a ½ saturated aqueous sodium bisulfite solution was added. After 30 minutes of further stirring, filtration, followed by drying at high vacuum afforded 3β-acetoxy-15α-bromo-19-formyloxy-14β-hydroxy-5α-card-20(22)-enolide; ir(KBr) 3425 (broad), 3295 (sharp), 3070 (weak), 1735, 1727, 1719, 1710, 1705, 1619, 1565, 1370, 1355, 1239, 1115, 1021, 901, 890, and 882 $cm^{-1}$; the ir-spectrum of a chloroform solution had a strong peak at 3570 instead of the peaks at 3425 and 3295 $cm^{-1}$.

EXAMPLE 18

When 11 mg of 3β,19-diacetoxy-5α-carda-14,20(22)-dienolide was subjected to reaction conditions which were essentially the same as those in the preceding example, filtration of the aqueous suspension gave 3β,19-diacetoxy-15α-bromo-14β-hydroxy-5α-carda-(20(22)-enolide; uv (MeOH)217 mμ; ir (NUJOL), 3470 (broad), 3390 (weak), 3360 (weak), 3090 (weak), 1769, 1735, 1720, 1620, 1450, 1368, 1355, 1237, 1025, 951, 880 and 865 $cm^{-1}$.

EXAMPLE 19

A mixture, prepared by addition of a freshly made solution of 180 mg of N-bromoacetamide in 3.0 ml of water to 6.0 ml of acetone and 150 mg of 3β-acetoxy-19-formyloxy-5α-carda-14,20(22) -dienolide, was stirred in the dark under nitrogen with external cooling by an ice-bath for 2 hours whereupon 90 ml of ice-water and 6.0 ml of a half-saturated aqueous sodium bisulfite was added and stirring was continued for another hour. Filtration gave 3β-acetoxy-15α-bromo-19-formyloxy-14β-hydroxy-5α-card-20(22)-enolide, which was dissolved in 30 ml of methylene chloride and shaken for 16 hours with a mixture of 3.0 ml of pivalic acid-methylene chloride 1:10, 60 ml of water and Raney nickel; the latter had been freshly prepared from 9.0 g of a 50% nickel-aluminum alloy. Addition of ether-methylene chloride 4:1, followed by filtration through filter-pulp, extraction of the organic phase with half-saturated aqueous sodium bicarbonate and water, drying with sodium sulfate and evaporation at reduced pressure, combination of the crude product obtained with that of another reaction in which 50 mg of 3β-acetoxy-19-formyloxy-5α-carda-14,20(22) -dienolide were used as the starting material, and several recrystallizations of the combined products from ether-hexane gave 50.65 mg of product, mp 232,234°-239°. Further purification of 24 mg of this material by chromatography on Silica gel G coated glass plates with ethyl acetate-benzene 1:2 as the eluant gave 19 mg of a fraction, which after recrystallization from ether-hexane yielded 16.76 mg of purified coroglaucigenin 3-acetate 19-formate, mp 248.5°-250.2° C. The mother liquors, when subjected to chromatography as described above, afforded further amounts of the latter compound as well as several fractions amounting to approximately 20 mg of 3β-acetoxy-19-formyloxy-14β-,15β-oxido-5α-card-20(22)-enolide.

EXAMPLE 20

When 15α-bromo-3β,19-diacetoxy-14β-hydroxy-5α-card-20(22)-enolide, which had been freshly prepared from 11 mg of 3β,19-diacetoxy-5α-carda-14,20(22)-dienolide as described in Example 18, was treated under reaction conditions, which were essentially similar to that described in the preceding example except that the reduction with Raney Nickel was carried out in an atmosphere of hydrogen instead of nitrogen, chromatography of the crude product on silica gel G coated glass plates with ethyl acetate-benzene 1:2 as the eluant, followed by recrystallization from ether-pentane, gave 3β,19-diacetoxy-14β-hydroxy-5α-card-20(22)-enolide (coroglaucigenin diacetate), mp 207°-212° C.; coroglaucigenin diacetate prepared by A. Hunger and t. Reichstein, Helv., 35, 1073 (1952) p.1097 from coroglaucigenin had mp 210°-214° and 216°-219° C.

EXAMPLE 21

3β-Acetoxy-19-formyloxy-15α-bromo-14β-hydroxy-5α-card-20(22)-enolide was prepared from 25 mg of 3β-acetoxy-19-formyloxy-5α-carda-14,20(22)-dienolide as described in Example 17. A methanolic solution of the freshly filtered bromohydrin was then stirred with a molar excess of concentrated aqueous ammonia at room temperature under nitrogen for several hours and then left at −5° C for 16 hours, whereupon the base was neutralized with acetic acid in ethyl acetate and the mixture was evaporated at reduced pressure. The residue obtained was extracted 3 times with ether-methylene chloride 4:1 and the combined extracts were chromatographed graphed on silica gel G coated glass plates using ethyl acetate-benzene 1:2 as the eluant. Recrystallization of the major fraction from ether-hexane gave 11.36 mg of 3β-acetoxy-19-formyloxy-14β,15β-oxido-5α-card-20(22)-enolide mp 213°–215° C.

EXAMPLE 22

A mixture, consisting of 15α-bromo-3β,19-diacetoxy-14β-hydroxy-5α-cardenolide, which had been freshly prepared from 2.6 mg of 3β,19-diacetoxy-5α-carda-14,20(22)-dienolide, by the method described in Example 17, and 0.13 ml of t-butylamine was left to stand under nitrogen for 30 minutes whereupon it was evaporated at reduced pressure. Treatment of the residue with ether and water, repeated extraction of the organic phase with water, evaporation and recrystallization from ether-pentane gave 3β,19-diacetoxy-14β,15β-oxido-5α-card-20(22)-enolide, mp 194, 200°–204° C.

EXAMPLE 23

A mixture, consisting of 3β-acetoxy-19-formyloxy-15α-bromo-14β-hydroxy-5α-card-20(22)-enolide, which had been freshly prepared from 20 mg of 3β-acetoxy-19-formyloxy-5α-carda-14, 20(22)-dienolide as described in Example 17 and was still wet, 1 ml of t-butylamine and 0.5 ml of water was stirred for 1 hour in an atmosphre of nitrogen, whereupon it was concentrated at reduced pressure with intermittent addition of hexane and water. Filtration yielded 8.0 mg of crude 3β-acetoxy-19-hydroxy-14β, 15β-oxido-5α-card-20(22)-enolide. Recrystallization from hexane-methylene chloride gave the purified sample, mp 227°–229° C.

EXAMPLE 24

A mixture, consisting of 7 ml of methanol and crude 3β-acetoxy-19-formyloxy-14β-hydroxy-5α-card-20(22)-enolide, prepared from 150 mg of 3β-acetoxy-19-formyloxy-5α-carda-14,20(22)-dienolide as described in Example 19, was stirred under nitrogen at room temperature; 4.9 ml of methanol-2% aqueous potassium hydroxide 20:1 was then added during ½ hour. After 2 hours 0.245 ml of glacial acetic acid-ethyl acetate 1:50 was added and the mixture was evaporated at reduced pressure. Extraction of the residue with ethermethylene chloride 4:1, followed by extraction of the organic phase with water, drying with sodium sulfate evaporation and chromatography on silica gel G coated glass plates with ethyl acetate-benzene 1:1 as the eluant gave 37 mg of 3β-acetoxy-14β,19-dihydroxy-5α-card-20(22)-enolide (coroglaucigenin 3-acetate), mp 233°–234°.

EXAMPLE 25

Oxidation of 4 mg of coroglaucigenin 3-acetate with t-butyl chromate in t-butanol-carbon tetrachloride 1:6 by a method which was essentially the same as the one described by A. Katz, Helv. 35, 487 (1957), p.490, gave corotoxigenin 3-acetate, mp 200, 221°–229°, after recrystallization of the crude product with ether-hexane. The irspectrum of the latter compound was identical to that obtained by A. Hunger and T. Reichstein, Helv. 35, 1073 (1952), who obtained corotoxigenin 3-acetate, mp 227°–234° and 200°–230° from corotoxigenin. The t-butyl chromate was prepared as described by K. Hensler and A. Wettstein, Helv., 35, 284 (1952).

EXAMPLE 26

A mixture of 6 mg of coroglaucigenin 3-acetate 19-formate, 0.3 ml of t-butylamine and 0.3 ml of water was shaken under nitrogen at room temperature for 24 hours whereupon it was evaporated at reduced pressure with intermittent addition of glacial acetic acid-water 5:1. The residue was disintegrated in 0.2 ml of water and the resulting suspension was filtered. The precipitate was recrystallized from methanol-ether yielding 3.7 mg of crude coroglaucigenin, mp 227°–230° . Chromatography on silica gel G coated glass plates with ethyl acetate as the eluant, followed by recrystallization from methanol-ether, gave the purified sample; mp 241°–242°, 244°; ir(KBr) max. 3610, 3350 3098, 1781, 1750, 1738, 1620, 1445, 1370, 1339, 1309, 1301, 1175, 1148, 1135, 1075, 1035, 1025, 1019, 959, 891, 887, 880, 869, 790, 780, 741 and 698 cm$^{-1}$.

EXAMPLE 27

A mixture, consisting of 45 mg of 3β-acetoxy-carda-5,20(22)-dienolide, 9.0 ml of methanol and 0.9 ml of 2% aqueous potassium hydroxide was stirred for 4 hours whereupon another lot of 0.9 ml of 2% aqueous potassium hydroxide was added. The mixture, in which a precipitate had formed was left to stand at −5° C for 16 hours and was then filtered. The precipitate was washed with water-methanol 1:3 and then with water. The filtrate was concentrated and filtered yielding a second precipitate. Both precipitates were combined and chromatograhed on silica gel G coated glass plates using ethyl acetate-benzene 1:4 as the eluant. The fraction having rf 0.2–0.3 was recrystallized from ether-hexane and yielded 5.7 mg of 3β-hydroxy-carda-5,20(22)-dienolide, ir(KBr) 3460 (broad),1805, 1730, 1620, 1190, 1170, 1135, 1108, 1070, 1052, 1030, 985, 965, 905, 870, 812, 745 and 712 cm$^{-1}$.

The latter 3β-hydroxycardenolide was also obtained, as indicated by tlc analysis, when the 3β-[diethylphosphono]-acetoxy analog of the starting material was similarly hydrolysed with methanol and 2% aqueous potassium hydroxide.

EXAMPLE 28

When 25 mg of 19-formyloxy-5α-carda-14,20(22)-dienolide was oxidized with N-bromo acetamide as outlined in Example 17, the corresponding 14β-hydroxy-15α-bromo analog was obtained. The freshly filtered and still wet bromohydrin, when reduced with Raney nickel as described in Example 17, gave a crude product which was purified by chromatography on silica gel G coated glass plates with ethyl acetate-benzene 1:1 as the eluant. Recrystallization of the fraction having rf 0.3–0.4 from ether-hexane gave 8.4 mg of 14β,19-dihydroxy-5α-card-20(22)-enolide 19-formate, mp 195°–198° C, ir(KBr) 3565, 3415 (broad), 3330 (shoulder), 3090 (small) 1785, 1755, 1742, 1737, 1730, 1721, 1715, 1628 and 1175 cm$^{-1}$. A less polar fraction isolated was recrystallized from hexane-methylene chloride are yielded 19-formyloxy-14,15β-oxido-5α,14β-cardenolide, mp 190°–192° C.

EXAMPLE 29

A freshly prepared mixture, consisting of 11.2 ml of anhydrous tetrahydrofuran, 0.187 ml of redistilled ethoxyacetylene and 1.12 ml of 1.95M methyl lithium in ether was added to a solution of 50 mg of 3β-acetoxy-21-hydroxy-8,19-oxido-5α-pregn-14-en-20-one in 8.7 ml of tetrahydrofuran which was protected by an atmosphere of nitrogen. After stirring under nitrogen for 4 hours the solvents were evaporated at reduced pressure. The residue was treated with wet ether and the ethereal phase was extracted several times with water till the aqueous extracts were no longer basic. Evaporation yielded a resin consisting mainly of 20-ethoxyethynyl-3β,20, 21-trihydroxy-8,19-oxido-5α-pregn-14-ene as evidenced by tlc analysis and the subsequent transformations. The latter product was then vigorously stirred with 3.5 ml of benzene and 1.75 ml of 2N aqueous sulfuric acid under nitrogen for 4 hours, whereupon the reaction mixture was diluted with benzene, and extracted successively with water and half saturated aqueous sodium bicarbonate. The benzene solution was dried over sodium sulfate and filtered through a column of 70 mg of aluminium oxide. Washing of the column with ethyl acetate afforded 21 mg of a product, which solidified with hexane and consisted essentially of 3β-hydroxy-8,19-oxido-5α-carda-14,20(22)-dienolide. Subsequent standing with 0.084 ml of pyridine and 0.042 ml of acetic anhydride for 20 hours in a nitrogen atmosphere, followed by addition of 20 volumes of water, extraction with ether, extraction of the ethereal phase with water and evaporation afforded the corresponding 3-acetate, which was then reduced with zinc and formic acid in presence of toluene under conditions which were similar to those described in Example 14. Chromatography of the total product obtained on silica gel G coated glass plates with ethyl acetate-benzene 1:4 as the eluant gave 9.7 mg of 3β,19-dihydroxy-5α-carda-14,20(22)-dienolide 3-acetate 19-formate as a white solid, which had an ir spectrum identical to the product of Example 13.

When 3β,21-dihydroxy- or 3β21-diacetoxy-8,19-oxido-5α-pregn-14-ene instead of 3β-acetoxy-21-hydroxy-8,19-oxido-5α-pregn-14-ene were reacted with ethoxyacetylene as described above, 20-ethoxyethynyl-3β,20, 21-trihydroxy-8,19-oxido-5αpregn-14-ene was obtained.

EXAMPLE 30

When 3β-acetoxy-8,19-oxido-5α-pregn-14-en-20-one was reacted with ethoxyacetylene as described in the preceding example, a compound considered to be 20-ethoxyethynyl-3β,20-dihydroxy-8,19-oxido-5α-pregn-14-ene was obtained; similarly 8,19-oxido-3β-[tetrahydropyran-2-yloxy]-5α-pregn-14-en-20-one gave a compound considered to be 20-ethoxyethynyl-20-hydroxy-8,19-oxido-3β-tetrahydropyran-2-yloxy-5α-pregn-14-ene. The latter two ethoxyacetylene adducts, when treated with aqueous sulfuric as described in the preceding example, gave ethyl 3β-hydroxy-8,19-oxido-24-nor-5α-chol-20(22)-en-23-oate, uv max. 222 mμ, as evidenced by tlc analysis.

EXAMPLE 31

When 32 mg of 14β-hydroxy-3β-[pyran-2-yloxy]-8,19-oxido-5α-pregnan-20-one was reacted with ethoxyacetylene similarly as described in Example 29, a product containing 20-ethoxyethynyl-3β,14β-dihydroxy-8,19-oxido-5α-pregnan-20-one was obtained, which after treatment with aqueous sulfuric acid, similarly as described in Example 29 except that ethanol was used as the solvent, gave a product containing ethyl 3β,14β-dihydroxy-8,19-oxido-24-nor-5α-chol-20(22)-en-23-oic acid. Acetylation with acetic anhydride-pyridine 1:2 followed by chromatography of the crude product on silica gel G coated glass plates with ethyl acetate-benzene 1:4 as the eluant gave ethyl 3β-hydroxy-8,19-oxido-24-nor-5α-chol-20(22)-en-oate, uv max. 231 mμ, treatment of this product with selenium dioxide in boiling benzene as described by N. Danieli, Y. Mazur and F. Sondheimer, J. Am. Chem. Soc., 84, 875 (1962) followed by chromatography on silica gel G coated glass plates with ethyl acetate-benzene 1:4 as the eluant gave a fraction considered to be 8,19-oxidouzarigenin acetate, uv max. 218 mμ. A further, more polar fraction had also uv max. 218 mμ and was considered to be 14α-hydroxy-8,19-oxidouzarigenin 3-acetate (cf F. Sondheimer, Chemistry in Britain, 1, 454 (1965), p. 459).

EXAMPLE 32

A mixture of 200 mg of 3β-acetoxy-21-hydroxypregn-5-en-20-one, 10 ml of methyl isobutyl ketone, 2.0 g of malonic acid and 2.0 g of calcium chloride was heated under nitrogen at 84° C. for 2 days, whereupon it was evaporated at reduced pressure with intermittent addition of benzene. The residue obtained was treated with water and p the resulting precipitate was filtered and washed well with water. The precipitate was dissolved in methylene chloride and the solution was concentrated with intermittent addition of pentane. The supernatant petroleum ether phase was decanted and the precipitation from pentane was repeated twice. The remaining residue was dissolved in ethermethylene chloride, treated with charcoal and filtered through diatomaceous earth. Concentration of the filtrate at reduced pressure with intermittent addition of hexane and ether, followed by filtration, gave 192 mg of 3β,21-dihydroxypregn-5-en-20-one 3-acetate 21-hemimalonate.

A solution of the latter compound in ether-diazotoluene, which was prepared by mixing briefly 22.3 mg of N-benzyl-N'-nitro-N-nitrosoguanidine, 0.040 ml of potassium hydroxide-water 1:1 and 1 ml of ether with external cooling by an ice-acetone bath, was then left to stand at −50° C. for 15 minutes. Evaporation at reduced pressure gave an off-white solid consisting mainly of 3β-acetoxy-21-[bensyloxycarbonyl]acetoxypregn-5-en-20-one. Treatment of part of the latter product with 20 parts t-butylamine for 25 minutes at room temperature, followed by evaporation, gave a product consisting mainly of 3β-acetoxy-22-[benzyloxycarbonyl]-carda-5,20(22)-dienolide as evidenced by tlc analysis.

EXAMPLE 33

A mixture of 200 mg of 3β-acetoxy-21-hydroxypregn-5-en-20-one, 10 ml of dimethyl malonate and 2.0 g of calcium chloride was heated in an oil-bath having a temperature of 84° C. for 4 days under nitrogen whereupon 20 ml of toluene was added. The reaction was then arranged for distillation at atmospheric pressure and the bath temperature was raised to 160° C. during 1.5 hours. Subsequently the temperature of the bath temperature was lowered to 84° and the mixture was subjected to distillation at high vacuum for 1.5 hours. The resulting solid residue was dissolved in 15 ml of ether, 2.5 ml of hexane and some charcoal was added. Filtration through diatomaceous earth, followed by concentration of the filtrate with intermittent addition of hexane and ether gave a suspension which after filtration gave 3β-acetoxy-21-[methoxycarbonyl]acetoxypregn-5-en-20-one.

EXAMPLE 34

A mixture of 220 mg of the product of the preceding Example and 2.2 ml of t-butylamine-benzene 1:10 was left to stand at room temperature under nitrogen for 35 minutes, whereupon it was concentrated at reduced pressure with intermittent addition of benzene. Hexane was then added till the solution became slightly turbid. Subsequent filtration through diatomaceous earth and concentration of the filtrate at reduced pressure with intermittent addition of hexane gave resinous precipitate, which was dissolved in ether and precipitated from hexane. The precipitation from hexane was repeated once more yielding finally 127 mg of a beige solid consisting mainly of 3β-acetoxy-22-methoxycarbonylcarda-5,20(22)-dienolide. Chromatography on silica gel G coated glass plates with ethyl acetate-benzene 1:6 as the eluant, followed by recrystallization from hexane gave a purified sample, mp 100, 112°–120°, uv (MeOH) 229 mμ; ir(KBr) 1770, 1725, 1655, 1240 and 1030 cm$^{-1}$. A methanolic solution of the sample, after addition of a small amount of aqueous potassium hydroxide, rapidly changed from uv 229 to 235, 286 (major) mμ. During the chromatographic development a pink colour, which appears typical for 22-[alkyloxycarbonyl]-card-20(22)-enolides, developed.

EXAMPLE 35

A mixture, prepared by addition of 0.1875 ml of anhydrous tetrahydrofuran to 30 mg of methyl[diethylphosphono]-acetate, cooling in an ice-bath, addition of 2.2 mg of sodium hydride-mineral oil 1:1, warming to room temperature and addition of 27.75 mg of 21-hydroxy-6,19-oxidopregn-4-en-3-one, was stirred at room temperature for 20 hours, whereupon a mixture of 30 mg of methyl [diethylphosphono]acetate. 0.1875 ml of anhydrous tetrahydrofuran and 2.2 mg of sodium hydride-mineral oil 1:1 was added and stirring was continued for another 2 hours. Evaporation at reduced pressure followed by addition of 5 ml of ethyl acetate, 5 extractions with water and evaporation of the extracted organic phase at reduced pressure gave a product which, after chromatography on silica gel G coated glass plates with ethyl acetatebenzene 1:1 as the eluant and recrystallisation of the fraction having rf 0.35 from ether-pentane gave 3-oxo-6,19-oxidocarda-4,20(22)-dienolide, uv(MeOH) 225 (broad) mμ which had an ir spectrum identical to that of the product of Example 7.

EXAMPLE 36

A mixture was prepared by successive addition, against a stream of nitrogen, of 76 mg of sodium hydride-mineral oil 1:1, a solution of 0.340 ml of [diethyophosphono]-acetonitrile in 1.2 ml of tetrahydrofuran and 73 mg of 5α-chloro-3β,21-diacetoxy-6,19-oxidopregnan-20-one in 6 ml of tetrahydrofuran to 5.2 ml of tetrahydrofuran; during the additions the reaction vessel was cooled by an ice-bath. The ice-bath was then removed and the mixture was stirred under nitrogen at room temperature for 20 hours. One half of the reaction mixture was then evaporated at reduced pressure and the residue obtained was left to stand with 5.7 ml of 2N aqueous hydrochloric acid in the refrigerator overnight. The precipitate which had formed was filtered off and washed with water and ether yielding 3β-acetoxy-5α-chloro-6,19-oxido-23-iminocard-20(22)-enolide hydrochloride, uv(MeOH) 237 mμ, ir(KBr) 3375, 1735, 1675, 1605, 1450, 1370, 1245, 1230, 1095, 1035, 1025 and 920 cm$^{-1}$.

A fraction amounting to ¼ of the original reaction mixture was then evaporated and the residue obtained was treated with 0.57 ml of concentrated hydrochloric acid and 0.57 ml of ether with external cooling. Heating of the separated acidic aqueous phase at 70° C. under nitrogen and subsequent filtration gave 5α-chloro-3β-hydroxy-6,19-oxidocard-20(22)-enolide, uv(MeOH) 218 mμ, ir(KBr) 3430 (broad), 1775, 1750, 1725, 1620, 1170, 1050, 1030, 1025, 1000, 920, 860 and 795 cm$^{-1}$.

EXAMPLE 37

When 33.4 mg of 5α-chloro-3β,21-diacetoxy-6,19-oxidopregn-20-one was subjected for 21 hours to the reaction condition of the preceding Example, evaporation of the reaction mixture at reduced pressure followed by treatment of the residue obtained with ether and 2N aqueous hydrochloric acid and evaporation of the ethereal phase gave a material, uv (MeOH) 222 mμ, which contained 3β,21-diacetoxy-5α-chloro-20-cyanomethylene-6,19-oxidopregnane as the major steroid, as evidenced by tlc analsyis.

EXAMPLE 38

A mixture of 130 mg of 3β-acetoxy-8,19-oxido-5α-22-[benzyloxycarbonyl]carda-14,20(22)-dienolide, 3.9 g of zinc dust, 9.75 ml of toluene and 3.25 ml of 90% formic acid was shaken for 16 hours under nitrogen, whereupon an additional lot of 3.9 g of zinc and of 1.3 ml of 90% formic acid was added. After 2 days of further shaking the supernatant liquid phase was decanted, 7.5 ml of benzene-methylene chloride 1:1 was added to the remaining residue, the mixture was shaken briefly and the supernatant liquid was decanted. After 4 further extractions with benzene-methylene chloride 1:1 and 5 subsequent extractions with methylene chloride the combined supernatant liquids were evaporated at reduced pressure. Dissolution of the resulting residue, followed by addition of pentane till a faint turbidity appeared, filtration through diatomaceous earth, concentration of the filtrate at reduced pressure with intermittent addition of pentane, standing at −5° C for 30 minutes, decantation of the supernatant liquid and drying at high vacuum gave 111 mg of a residue which contained 3β-acetoxy-22-benzyloxycarbonyl-19-formyloxy-24-nor-5α-chola-14,20(22)-dien-23-oic acid (probably as the olefinic Z-isomer) and also 3β-acetoxy-22-benzyloxycarbonyl-19-formyloxy-5α-carda-14,20(22)-dienolide as evidenced by tlc.

Heating of 100 mg of the residue between 110 to 125° C in an evacuated tube for 225 minutes followed by chromatographic separation on silica gel G coated glass plates with ethyl acetate-benzene 1:20 as the eluant gave 35 mg of 3β-acetoxy-19-formyloxy-24-nor-5α-chol-20(22)-en-23-oic acid (probably the olefinic Z-isomer) as a colourless resin; uv (MeOH) 218 and 227 (shoulder; no change after basification of the methanolic sample solution with potassium hydroxide) mμ; nmr (CDCl$_3$) 8.16, 7.40, 6.55, 5.84, 5.18, 5.08, 4.4, 3.13, 2.01 and 0.78 ppm; m/e 534, 443 and 337. The chromatographic separation also yielded, as the more polar fraction, 15 mg of 3β-acetoxy-19-formyloxy-22-benzyloxycarbonyl-5α-carda-14,20(22)-dienolide; m/e 576 (weak), 485 (medium), 483 (medium) and 467 (strong); uv (MeOH) 216, 230 and 249 (minor peak) mμ, 288 (major peak) mμ after basification of the methanolic sample solution with aqueous potassium hydroxide.

EXAMPLE 39

A mixture of 300 mg of 3β-acetoxy-22-benzyloxycarbonylcarda-5,20(22)-dienolide, 9.0 g of zinc dust, 22.5 ml of toluene and 7.5 ml of 90% formic acid was shaken under nitrogen for 16 hours, whereupon an additional lot of 9 g zinc dust and 3.0 ml of 90% formic acid was added. Shaking was continued for 24 hours, whereupon yet another lot of 9 g of zinc dust and 3.0 ml of 90% formic acid was added. The mixture was then filtered, the precipitate was washed well with methylene chloride and the combined filtrates were evaporated at reduced pressure. The residue obtained was treated with methylene chloride and the resulting suspension was filtered. The filtrate was concentrated with intermittent addition of hexane and then left to stand at room temperature under nitrogen till the supernatant liquid had clarified. Decantation gave a residue containing mainly an acid considered to be (20(22)Z)-3β-acetoxy-22-benzyloxycarbonyl-24-nor-chola-5,20(22)-dien-23-oic acid in addition to some starting material. A mixture consisting of 4.0 ml of an ethereal solution of the latter compound and 4.0 ml of an ethereal solution of diazomethane was then left to stand at 0° C for 20 minutes. Subsequent tlc analysis indicated that still substantial amounts of the steroidal carboxylic acid remained and an additional 4 ml of the ethereal diazomethane solution was added. The mixture was then left to stand at 0° C for another 20 minutes, whereupon it was evaporated at reduced pressure. Chromatography of the greenish foam on silica gel G coated glass plates with ethyl acetate-benzene 1:20 gave 55 mg of a more polar fraction as a resin consisting of a mixture of methyl (20(22)Z)- and (20(22)E) acetoxy-22-benzyloxycarbonyl-24-norchola-5,20(22)-dien-23-oate; uv(MeOH) 213 and 235 ;l (unchanged after basification of the methanolic sample solution with aqueous potassium hydroxide) mμ; nmr (CDCl$_3$) 7.19, 5.21, 5.18, 5.1, 4.55, 3.55, 3,50, 2.5, 2.6, 1.0, 0.68, 0.59 and 0.59 ppm. The chramatography also afforded 6.6 mg of a less polar fraction as a resin, which was considered to be a diazomethane adduct of the above methyl enoates.

EXAMPLE 40

A solution of 60 mg of 3β-acetoxy-22-benzyloxycarbonylcarda-5,20(22)-dienolide in 12.0 ml of ethanol was stirred at room temperature in an atmosphere of hydrogen in presence of 6 mg of 5% palladium on charcoal for one hour, whereupon it was filtered through paperpulp in presence of nitrogen. Evaporation at reduced pressure gave a foam. A solution of 9/10 of the latter in 9 ml of ethanol was then stirred at room temperature in an atmosphere of hydrogen in presence of 6 mg of 5% palladium on charcoal for 50 minutes (rehydrogenation). Isolation of the steroidal material as outlined above and treatment of the residue obtained with etherhexane gave a white solid consisting essentially of 3β-acetoxy-22-carboxylcarda-5,20(22)-dienolide. A small fractiion of the latter product, when heated in an evacuated tube at 137°–142° for 20 minutes gave 3β-acetoxycardenolide as evidenced by tlc analysis.

EXAMPLE 41

A mixture of 40 mg of the product of the latter reaction, when treated repeatedly with zinc dust as described in Example 39, gave a product containing 2,2-[3β-acetoxypregn-5-en-20-ylidene]malonic acid. Subsequent treatment of the latter with 0.8 ml of ether and 2.4 ml of an ethereal diazomethane solution, which was freshly prepared as described in Aldrich Chemical Catalog 14, 1969–1970, at 0° for 1–2 hours, concentration at reduced pressure to ½ of the original volume, addition of hexane, further concentration with intermittent addition of hexane, evaporation and chromatography of the residue obtained on silica gel G coated glass plates, using ethyl acetate benzene as the eluant, gave a fraction which after recrystallisation from ether-hexane gave 2.5 mg of dimethyl 2,2-[3β-acetoxypregn5-en-20-ylidene]malonate, uv (MeOH) 219 and 232 (no change after addition of aqueous potassium hydroxide to the methanolic sample solution) mμ; m/e 412, 397, 380 and 365.

EXAMPLE 42

A mixture of 70 mg of 21-acetoxy-8,19-oxido-5β-pregn-14-en-20-one, 12.2 ml of anhydrous tetrahydrofuran and 17.6 ml of tetrahydrofuran-ethoxyacetylene — 1.95N methyl lithium in ether 11.2:0.245:1.12 was stirred under nitrogen for about 2 hours, whereupon it was evaporated at reduced pressure with minimal exposure to air. The residue was dissolved in 35 ml of ether and extracted five times with 17.5 ml of water in an atmosphere of nitrogen. Evaporation at reduced pressure gave a product considered to consist essentially of 20ξ,21-dihydroxy-20ξ-ethoxyethynyl-8,19-oxido-5β-pregn-14-ene, which was stirred for 40 minutes with 6.95 ml of ethanol and 1.39 ml of 2N aqueous sulfuric acid under nitrogen, whereupon 35 ml of water was added. Extraction of the aqueous mixture with ether and methylene chloride, followed by repeated extraction of the combined organic phases with water, evaporation and preparative thin layer chromatography (silica gel G, ethyl acetate - benzene 1:4) of the residue obtained gave 26.32 mg of a yellow solid consisting essentially of 8,19-oxido-5β-carda-14,20(22)-dienolide as evidenced by tlc analysis and by the reactions of the following Examples.

EXAMPLE 43

A mixture of 660 mg of zinc dust, 22 mg of 8,19-oxido-5β-carda-14,20(22)-dienolide, 1.65 ml of toluene and 0.55 ml of 90% formic acid was shaken at room temperature for 19 hours, whereupon 2.2 ml of ethyl acetate and 1.1 ml of water was added. Shaking was continued for 0.5 hours, whereupon the mixture was filtered. Repeated extraction of the filtrate with water, evaporation of the organic phase, preparative thin layer chromatography (silica gel G, ethyl acetate-benzene 1:4), extraction of the major product from the scraped silica gel powder with methanol-ethyl formate 4:1, evaporation of the extract at reduced pressure, treatment of the residue with methylene chloride, filtration and evaporation of the filtrate gave 16.22 mg of 19-formyloxy-5β,8β-carda-14,20(22)-dienolide as a white solid, which was used for the next reaction.

EXAMPLE 44

When 12 mg of 19-formyloxy-5β-carda-14,20-(22)-dienolide was oxidized with N-bromoacetamide under conditions which were essentially the same as those outlined in Example 17, the corresponding 14β-hydroxy-15α-bromo analog was obtained, the freshly filtered and still wet bromo hydrin was reduced with Raney nickel under the conditions described in Example 17. The crude product was purified by chromatography on silica gel G coated glass plates with ethyl acetatebenzene 1:4 as the eluant. The fraction, rf 0.45–0.5, 0.82 mg, was considered to consist of 19-formyloxy-14,15β-oxido5β,14β-card-20(22)-enolide. The fraction rf 0.20–0.25, 6.65 mg consisted of 19-formyloxy-14-hydroxy-5β,14β-card-22(22)-enolide and a small amount of an impurity of similar rf value. The latter fraction, 0.325 ml of methylene chloride, 195 mg of zinc dust and 0.65 ml of methylene chloride saturated with 90% formic acid was shaken under nitrogen for 55 minutes. Filtration, followed by dilution of the filtrate with ether, extraction of the organic phase with water, half-saturated aqueous sodium bicarbonate and water, evaporation of the organic solvent, chromatography of the residue as outlined above and recrystallisation of the major fraction with methylene-chloride-pentane gave 4.75 mg of purified 19-formyloxy-14-hydroxy-5β,14β-card-20(22)-enolide, mp 158°–158.5° C, ir(KBr) 3871, 3463, 3100, 2945, 2910, 2890, 2880, 1786, 1750, 1718, 1635, 1628, 1481, 1456, 1381, 1350, 1311, 1270, 1185, 1089, 1072; 1049, 1032, 991, 961, 912, 860 and 700 cm$^{-1}$; m/e 402, 384, 356 and 325.

I claim:

1. A compound of the formula

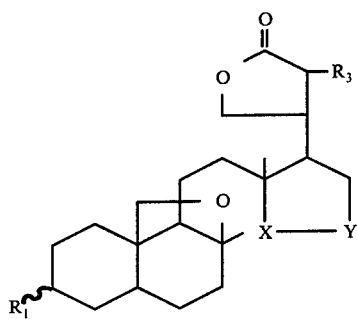

wherein $R_1$ is H, OH, O, O-acyl,

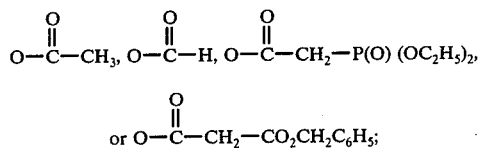

and $R_3$ is selected from the group consisting of H, $CO_2H$, $CO_2CH_2C_6H_5$, $CO_2CH_3$, $CO_2CH_2CH_2OH$ and CN; X-Y is C=CH or an α-oxide; and the Δ2, Δ3, Δ4, Δ5(6), Δ7 and Δ20(22) dehydro analogs thereof.

2. A compound of the formula

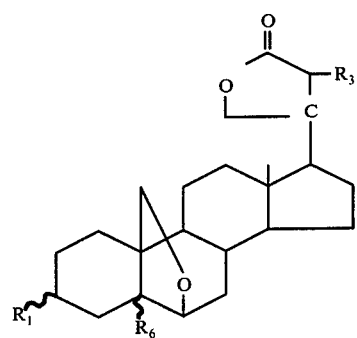

wherein $R_1$ is H, OH, O, O-acyl,

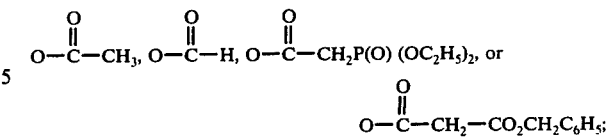

$R_6$ is H, Cl, Br or OH; $R_3$ is selected from the group consisting of H, $CO_2H$, $CO_2CH_2C_6H_5$, $CO_2CH_3$, $CO_2CH_2CH_2OH$ and CN; and the Δ2, Δ3, Δ4, and Δ20(22) dehydro analogs thereof.

3. A compound of the formula

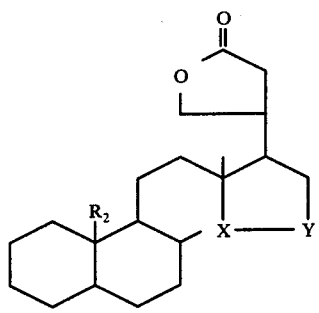

wherein $R_2$ is $CH_2OH$, CHO,

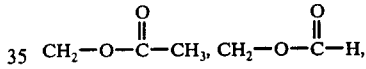

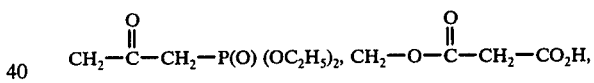

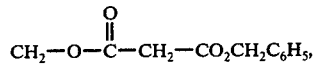

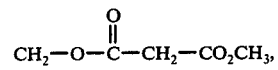

(HO) $(CH_3)CHCO_2CH_2$, $HO_2C(CHOH)_2CO_2CH_2$, $HO_2C(CH_2)_2CO_2$—$CH_2$, $HO_2CCH_2CO_2CH_2$, HC≡$CCH_2OCH_2$, tetrahydropyran2'-yloxymethyl, $CH_2Cl$, or

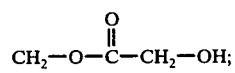

X-Y is C(β—OH)—$CH_2$, C(β-OH)-CHBr, C(β-OH)-CHCl, C(α-OH)-$CH_2$, a β-oxide, an α-oxide, C=CH,C(α-H)-$CH_2$ or C(β-H)-$CH_2$; and the Δ2, Δ3, Δ4, Δ5(6), Δ7, Δ8(9), Δ8(14) and Δ20(22) dehydro analogs thereof.

4. A compound of the formula

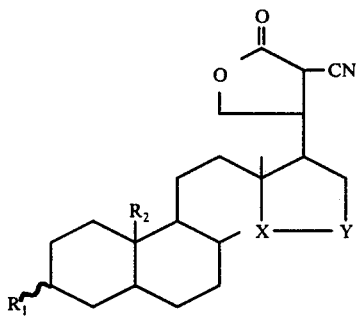

wherein $R_1$ is H, OH, O,

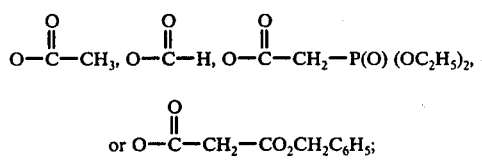

or $O-\overset{O}{\overset{\|}{C}}-CH_2-CO_2CH_2C_6H_5$;

$R_2$ is $CH_3$ or $CH_2OH$; and X-Y is $C(\alpha-H)-CH_2$, $C=CH$, or $C(\beta-OH)-CH_2$; and the $\Delta2$, $\Delta3$, $\Delta4$, $\Delta5(6)$, $\Delta7$, $\Delta8(9)$, $\Delta8(14)$ and $\Delta20(22)$ dehydro analogs thereof.

5. A compound of the formula

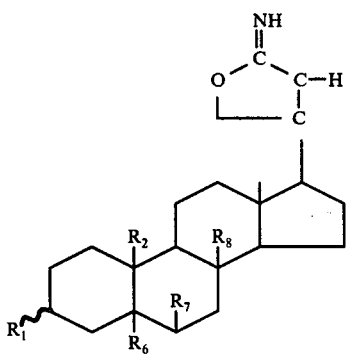

wherein $R_2$ and $R_8$ are an 8,19-oxido group or $R_2$ and $R_7$ are a 6,19-oxido group; $R_1$ is O, acetoxy or H; $R_6$ is H or Cl; and the $\Delta2$, $\Delta3$, $\Delta4$, $\Delta5(6)$, $\Delta7$, $\Delta8(9)$, $\Delta20(22)$ dehydro analogs thereof.

6. A compound of the formula

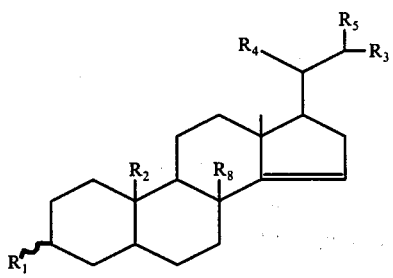

wherein $R_1$ is OH or OAc; $R_2$ together with $R_8$ is 8,19-oxido or $R_2$ is $CH_2OCOH$ or $CH_3$ and $R_8$ is H; $R_3$ is $CO_2$—lower alkyl, $CO_2$—$CH_2C_6H_5$ or $CO_2H$; $R_4$ is $CH_3$; $R_5$ is H, $CO_2H$, or $CO_2CH_3$; and the $\Delta5(6)$ and $\Delta20(22)$ dehydro analogs thereof.

7. A compound as defined in claim 1, wherein the steroid is selected from the group consisting of a carda-14,20(22)-dienolide or a carda-4,20(22)-dienolide.

8. A compound as defined in claim 1, wherein the steroid is a card-20(22)-enolide.

9. A compound as defined in claim 8, wherein the steroid contains a group selected from those containing of a 14,15$\beta$-oxido group, a 19-formyloxy group, a 14-hydroxy group, a 14$\beta$,19-dihydroxy group, a 3$\beta$-acetoxy group or a 3$\beta$,19-diacetoxy group.

10. A 3-deoxy steroid of claim 1, selected from group in which the substituent $R_1$ at the 3-position is a hydrogen atom.

11. A steroid of claim 10 which is selected from the group consisting of a 19-oxygenated-14-hydroxy-5$\alpha$,14$\beta$-card-20(22)-enolide or a 19-oxygenated-14-hydroxy-5$\beta$,14$\beta$-card-20(22)-enolide.

12. A process for preparing a compound of claim 1, said process comprising treating a compound of the Formula A

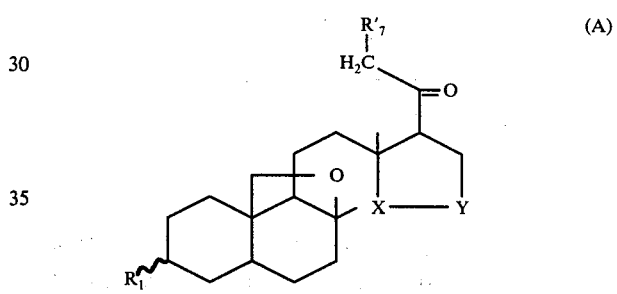

in which $R_1$ and X-Y are as defined in claim 1 and wherein $R'_7$ is OH with an $\alpha$-substituted acetic acid to form a compound of the Formula B

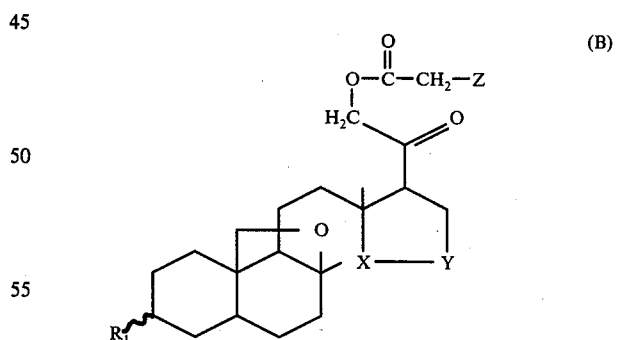

in which $R_1$ and X-Y are as in Formula A and wherein Z is a substituent chosen from those enhancing the acidity of the adjacent methylene group; and finally treating the compound of the Formula B with a base to form a compound of claim 19, or treating a compound of the Formula A in which $R'_7$ is OH, $OCOCH_3$ or H, with an alkali alkoxyacetylide and an alcohol or water to form an intermediate compound of the Formula

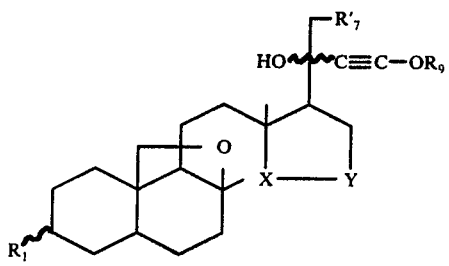

in which $R_1$ and X-Y are as in Formula A and in which $R_9$ is $C_2H_5$, $CH_3$ or $CH_2C_6H_5$, and subjecting said intermediate compound to acid treatment to form a compound of claim 19.

13. A process for preparing a compound of claim 2 comprising treating a compound of the Formula A

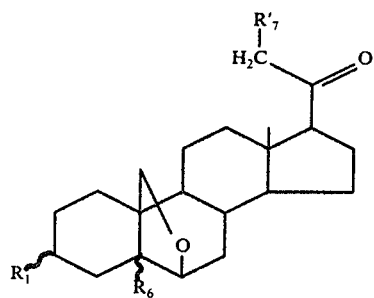

wherein $R'_7$ is OH and $R_1$ and $R_6$ are as defined in claim 2, with an α-substituted acetic acid to form a compound of the Formula B

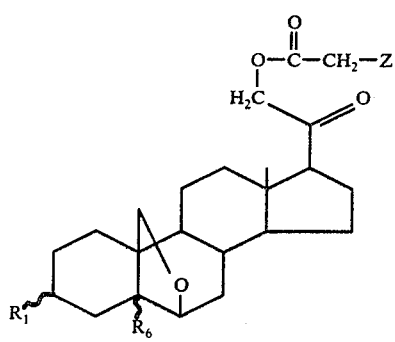

in which $R_1$ and $R_6$ are as in Formula A and wherein Z is a substituent chosen from those enhancing the acidity of the adjacent methylene group; and finally treating the compound of the Formula B with a base to form a compound of claim 2, or treating a compound of the Formula A in which $R_1$ and $R_6$ are as defined in claim 12 and wherein $R'_7$ is OH, OCOCH$_3$ or H, with an alkali alkoxyacetylide and an alcohol or water to form an intermediate compound of the Formula

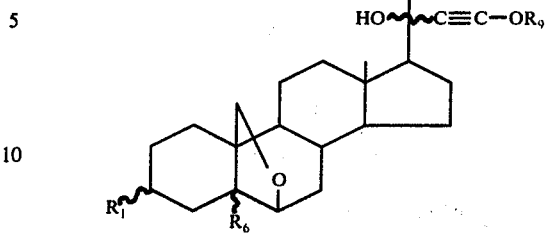

in which $R_1$, $R_6$ and $R'_7$ are as in Formula A and in which $R_9$ is $C_2H_5$, $CH_3$ or $CH_2C_6H_5$, and subjecting said intermediate compound to acid treatment to form a compound of claim 2.

14. A process for preparing a compound of claim 3 comprising treating the compound of Formula A

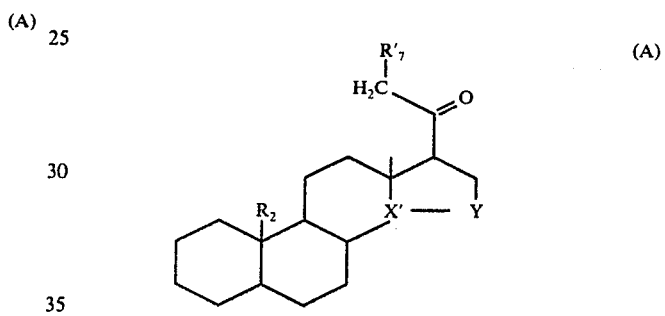

in which $R_2$ and X-Y are as defined in claim 3 and wherein $R'_7$ is OH, with an α-substituted acetic acid to form a compound of the Formula B

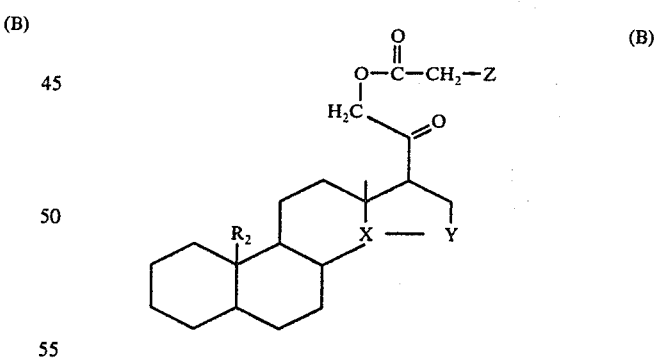

in which $R_2$ and X-Y are as defined in Formula A an wherein Z is a substituent chosen from those enhancing the acidity of the adjacent methylene group; and finally treating the compound of the Formula B with a base to form a compound of claim 21, or treating a compound of the Formula A in which $R_2$ and X-Y are as defined in claim 3 and in which $R'_7$ is OH, OCOCH$_3$ or H, with an alkali alkxyacetylide and an alcohol or water to form an intermediate compound of the Formula

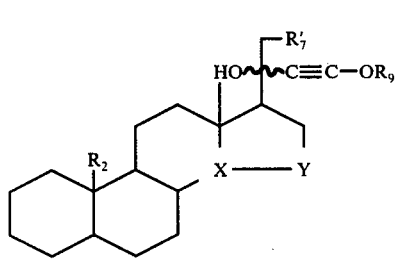

in which $R_9$ is $C_2H_5$, $CH_3$ or $CH_2C_6H_5$, and subjecting the latter compound to acid treatment to form a compound of claim 3.

15. A process for preparing a compound of claim 4 comprising treating a compound of the Formula A

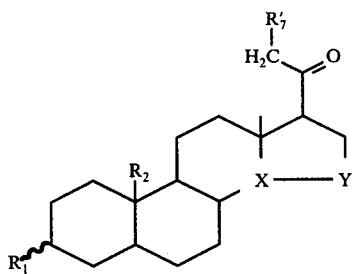

wherein $R'_7$ is OH, $R_1$, $R_2$ and X-Y are as defined in claim 22 with a cyano-substituted acetic acid to form a compound of the Formula B

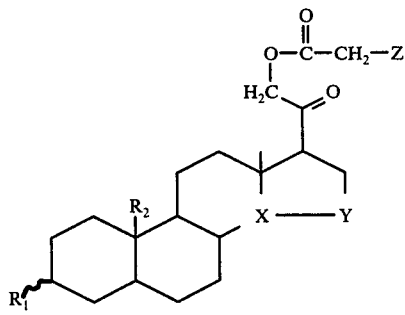

wherein $R_1$, $R_2$ and X-Y are as in Formula A and wherein Z is a cyano group, and treating the compound of Formula B with a base to form a compound of claim 4.

16. A process for preparing a compound of claim 6 comprising treating a compound of the Formula

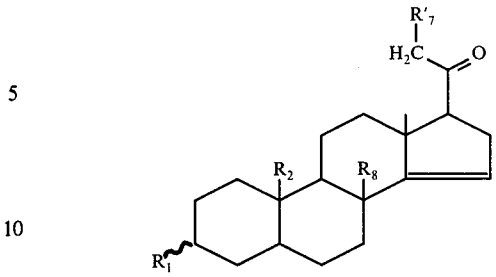

in which $R'_7$ is OH, $OCOCH_3$ or H, with an alkali alkoxyacetylide and an alcohol or water to form an intermediate compound of the Formula

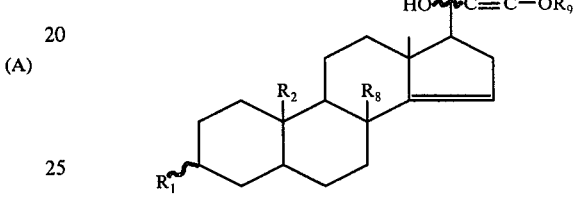

in which $R_9$ is $C_2H_5$, $CH_3$ or $CH_2C_6H_5$, subjecting the latter compound to acid treatment to form a compound of claim 6, or treating a compound similar to the compound of claim 6, but wherein $R_4$ and $R_5$ together represent $CH_2$-O and $R_3$ is as defined in claim 6, with zinc and a carboxylic acid to form a compound of claim 6 wherein $R_4$ and $R_5$ are separate and are as defined in claim 6.

17. A compound selected from the group consisting of 3β-acetoxy-8,19-epoxy-5α-carda-14,20(22)-dienolide; 3β-acetoxy-22-benzyloxycarbonyl-8,19-epoxy-5α-carda-14,20(22)-dienolide; 3β-acetoxy-22-cyano-8,19-epoxy-5α-carda-14,20(22)-dienolide; 22-cyano-3β-hydroxy-8,19-epoxy-5α-carda-14,20(22)-dienolide; 19-acetoxy-3-oxo-14α-carda-4,6,20(22)-trienolide; 3-oxo-8,19-epoxy-14α-carda-4,20(22)-dienolide; 3β-[(diethylphosphono) acetoxy]-14α-carda-5,20(22)-dienolide; 3β-acetoxy-22-cyano-14α-carda-5,20-(22)-dienolide; 3β-hydroxy-22-cyano-14α-carda-5,20(22)-dienolide; 8,19-epoxy-5α-carda-14,20(22)-dienolide; 19-hydroxy-5α-carda-14,20(22)-dienolide 19-formate; 3β-acetoxy-19-hydroxy-5α-carda-14,20(22)-dienolide; 3β-acetoxy-15α-bromo-19-formyloxy-14β-hydroxy5α-card-20(22)-enolide; coroglaucigenin 3-acetate 19-formate; 3β-acetoxy-19-formyloxy-14β,15β-epoxy-5α-card-20(22)-enolide; 3β-acetoxy-14β,19-dihydroxy-5α-card-20(22)-enolide; 14β,19-dihydroxy-5α-card-20(22)-enolide 19-formate; 19-formyloxy-14,15β-epoxy-5α,14β-card-20(22)-enolide; and 3-oxo-6,19-epoxy-14α-carda-4,20(22)-dienolide.

* * * * *